US010952981B2

(12) United States Patent
Dube et al.

(10) Patent No.: US 10,952,981 B2
(45) Date of Patent: Mar. 23, 2021

(54) LIQUID PHARMACEUTICAL COMPOSITIONS OF BACLOFEN FOR ORAL ADMINISTRATION

(71) Applicant: SLAYBACK PHARMA LLC, Princeton, NJ (US)

(72) Inventors: Sushant Omprakash Dube, Navi Mumbai (IN); Girish Kumar Jain, Hyderabad (IN); Venkateshwar Reddy Keesara, Hyderabad (IN); Josh Chandy Mathew, Princeton, NJ (US); Purushottam Dattatraya Kulkarni, Aurangabad (IN); Purushottam Sakhahari Pattewar, Hyderabad (IN); Balakrishna Reddy Akula, Hyderabad (IN); Kumarswamy Ummiti, Hyderabad (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 16/752,058

(22) Filed: Jan. 24, 2020

(65) Prior Publication Data

US 2020/0375932 A1  Dec. 3, 2020

(30) Foreign Application Priority Data

May 27, 2019  (IN) .............................. 201941020986

(51) Int. Cl.
*A61K 31/197* (2006.01)
*A61K 47/40* (2006.01)
*A61K 9/08* (2006.01)
*A61K 9/00* (2006.01)

(52) U.S. Cl.
CPC .......... *A61K 31/197* (2013.01); *A61K 9/0053* (2013.01); *A61K 9/08* (2013.01); *A61K 47/40* (2013.01)

(58) Field of Classification Search
CPC ............................. A61K 45/06; A61K 31/197
See application file for complete search history.

(56) References Cited

U.S. PATENT DOCUMENTS

| | | |
|---|---|---|
| 5,646,131 A | 7/1997 | Badwan et al. |
| 7,824,697 B2 | 11/2010 | Trissel et al. |
| 8,062,647 B2 | 11/2011 | Trissel et al. |
| 8,357,379 B2 | 1/2013 | Trissel et al. |
| 8,529,916 B2 | 9/2013 | Trissel et al. |
| 9,289,408 B2 | 3/2016 | Trissel et al. |
| 9,655,968 B2* | 5/2017 | Meythaler ............. A61K 9/0019 |
| 10,610,502 B1 | 4/2020 | Bryant et al. |
| 2004/0115258 A1 | 6/2004 | Stroppolo et al. |
| 2006/0105045 A1 | 5/2006 | Buchanan et al. |
| 2007/0020336 A1* | 1/2007 | Loftsson ................ A61K 31/42 424/486 |
| 2011/0021469 A1 | 1/2011 | Meythaler et al. |

FOREIGN PATENT DOCUMENTS

| | | |
|---|---|---|
| CN | 106389313 A | 2/2017 |
| WO | WO 2014/195394 A1 | 12/2014 |

OTHER PUBLICATIONS

Chou et al. CAS: 141:374644, 2004.*
International Search Report and Written Opinion of the International Searching Authority for International Application No. PCT/US2020/015632, dated Apr. 21, 2020.
Ahuja Analytical Profiles of Drug Substances and Excipients, Academic Press, vol. 14, 1985, 2 pages, abstract only.
Allen et al., "Stability of baclofen, captopril, diltiazem hydrochloride, dipyridamole, and flecainide acetate in extemporaneously compound orl liquids", AM J Health-Syst Pharm, vol. 53, Sep. 15, 1996, pp. 2179-2184 (6 pages).
Johnson et al., "Stability of an Extemporaneously Compound Baclofen Oral Liquid", American Journal of Hospital Pharmacy, vol. 50, No. 11, Nov. 1, 1993, pp. 2352-2355 (6 pages), abstract only.
Ahuja et al., Analytical Profiles of Drug Substances and Excipients, Academic Press, 1985, 1 pages, abstract only.
Allen et al., "Stability of baclofen, captopril, diltiazem hydrochloride, dipyridamole, and flacalnide acetate in extemporaneously compound oral liquids", AM J Health-Syst Pharm, vol. 53, Sep. 15, 1996, pp. 2179-2184 (6 pages).
Author Unknown, "KEMSTRO™ (baclofen orally disintegrating tablets) prescription label", NDA 21-589, date unknown, Oct. 30, 2003, 6 pages.
Author Unknown, OZOBAX™ (baclofen) oral solution, Highlights of Prescribing Information, Reference ID: 4493887, Revised: Sep. 2019, 7 pages.
Cruaud et al., "The characterization and release kinetics evaluation of baclofen microspheres designed for intrathecal injection", International Journal of Pharmaceutics, vol. 177, 1999, pp. 247-257 (11 pages).
Johnson et al., "Stability of an Extemporaneously Compounded Baclofen Oral Liquid", American Journal of Hospital Pharmacy, vol. 50, No. 11, Nov. 1, 1993, pp. 2352-2355 (6 pages), abstract only.

* cited by examiner

*Primary Examiner* — Rei Tsang Shiao
(74) *Attorney, Agent, or Firm* — Birch, Stewart, Kolasch & Birch, LLP

(57) ABSTRACT

The present invention relates to liquid pharmaceutical compositions of baclofen or a pharmaceutically acceptable salt thereof. More specifically, stable liquid pharmaceutical compositions of baclofen at concentrations of 5 mg/mL or more are provided. Preferably, the liquid pharmaceutical compositions are suitable for oral administration, and stable at pH ranges of 5-8 over a variety of storage conditions, including long-term storage for extended periods of time.

14 Claims, No Drawings

LIQUID PHARMACEUTICAL COMPOSITIONS OF BACLOFEN FOR ORAL ADMINISTRATION

CROSS-REFERENCE TO RELATED APPLICATIONS

This application claims foreign priority to Indian Application No. IN 2019/41020986, filed on May 27, 2019, which is incorporated herein by reference in its entirety.

FIELD OF THE INVENTION

The present invention relates to liquid pharmaceutical compositions of baclofen or a pharmaceutically acceptable salt thereof. More specifically, stable liquid pharmaceutical compositions of baclofen at concentrations of 5 mg/mL or more are provided. Preferably, the liquid pharmaceutical compositions are suitable for oral administration, and stable at pH ranges of 5-8 over a variety of storage conditions, including long-term storage for extended periods of time.

Methods of treating spasticity using the inventive pharmaceutical compositions are also provided. The invention further relates to various methods for preparing stable liquid pharmaceutical compositions of baclofen.

BACKGROUND OF THE INVENTION

Baclofen is a structural analog of the inhibitory neurotransmitter gamma-aminobutyric acid (GABA), and may exert its effects by stimulation of the GABA receptor subtype. Chemically, baclofen is 4-amino-3-(4-chlorophenyl)-butanoic acid, a derivative of Y-aminobutyric acid. It is represented by the following formula:

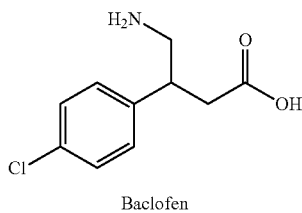 [SMILES: NCC(CC(=O)O)c1ccc(Cl)cc1]

Baclofen

Baclofen is a white to off-white, odourless or practically odourless crystalline powder, with a molecular weight of 213.66 g/mole. It is slightly soluble in water, very slightly soluble in methanol, and insoluble in chloroform. Its low solubility in water makes it difficult to obtain stable aqueous solutions of baclofen with concentrations greater than 2 mg/mL, and specifically greater than or equal to 5 mg/mL.

Baclofen is a skeletal muscle relaxant used to treat spasticity in conditions such as multiple sclerosis or spinal cord injury. Baclofen is currently approved and marketed as intrathecal injection, oral disintegrating tablet and tablet dosage forms. KEMSTRO® (oral disintegrating tablet) and LIORESAL® (tablet) were approved in United States for the alleviation of signs and symptoms of spasticity resulting from multiple sclerosis, particularly for the relief of flexor spasms and concomitant pain, clonus, and muscular rigidity. Baclofen intrathecal injection is approved for use in the management of severe spasticity in adult, geriatric, and pediatric patients from age 4 years and above.

Administration of solid oral dosage forms to pediatric and geriatric population still remains a challenge, particularly due to a frequent lack of age-appropriate formulations, which raises a concern about dose accuracy. Moreover, several factors specific to the pediatric and geriatric population, such as the ability to swallow, palatability issues, etc., may hamper the administration of oral medication. Indeed, most commercially available medicines are designed for adults and do not provide ease of use for pediatric and geriatric population. Beyond the efforts of health authorities to promote the development of pediatric and geriatric medicines, many medicinal products are authorized only for adults and are not currently available in formulations suitable for administration to pediatric and geriatric population. Consequently, caregivers or parents frequently modify medicines used off-label before administration in children, leading to dose error risk or inaccurate dosing, as well as stability and/or bioavailability issues pertaining to the drug.

In general, there is a need for developing oral liquid formulations of baclofen that allow for dosing flexibility which can cater to the needs of geriatric and pediatric population. There is an increased recognition that for medicines requiring precise dosage and titration, as with baclofen, development of oral formulations allow for tailored dosages across the dosing range, or for other populations with swallowing difficulties. In the absence of a ready-made product, there are several approaches that are utilized in an attempt to "create" an appropriate dosage form for pediatric and geriatric population. One frequent approach is to prepare an oral liquid from tablets, capsules or powdered drug dispersed or dissolved in a suitable base. The practice of crushing tablets or opening capsules and adding the powder to a drink (e.g., water, juice or soda) or sprinkling into solid food (e.g., apple sauce or pudding) is an alternative, but there are few circumstances where this method is appropriate. It is difficult to ensure that a complete dose has been taken, the effects on the drug from the food or drink the tablet is dispersed into are unknown, and the practice of nurses, caregivers or other healthcare professionals handling powdered drug may pose significant health concerns. With baclofen doses ranging from 1 mg to 400 mg per day, utilizing the currently available 5, 10, and 20 mg tablets presents significant challenges in drug delivery to the pediatric or geriatric population. For example, to deliver a 15 mg or any dose greater than 20 mg, multiple tablets and significant manipulation of the tablets is required to deliver these doses.

Baclofen dissolves poorly in water, and once dissolved, has a tendency to precipitate out of solution under normal storage conditions. Particularly at higher concentrations, baclofen may not completely dissolve in aqueous solution, or it may have an unacceptable tendency to precipitate out of solution during storage. Moreover, achieving long-term stability of baclofen in an oral solution is difficult and challenging.

Baclofen is also extemporaneously compounded as oral suspensions in the hospital pharmacies at concentrations of equal to or more than 5 mg/mL. However, sedimentation of solids is a common problem which is encountered in suspension products, which leads to caking (formation of compact mass), making it difficult to dispense the suspension. The content of active ingredient depends to a large extent upon the re-dispersibility of the oral suspension product. This results in dose uniformity issues resulting in patients receiving the dose of baclofen more or less than the maximum recommended dose. The over dose of baclofen in patients may cause coma or with progressive drowsiness, light-headedness, dizziness, somnolence, accommodation disorders, respiratory depression, seizures, or hypotonia progressing to loss of consciousness. Moreover, the extemporaneously compounded oral suspensions of baclofen are not suitable for long-term storage.

It has been reported that baclofen could be dissolved in strongly acidic or strongly basic pH solutions. For example, Ahuja (1985) reported that concentrations of baclofen greater than 20 mg/mL could be obtained by dissolving baclofen in aqueous solutions of 0.1N HCl or aqueous solutions of 0.1N NaOH. However, at a very high and a very low pH, baclofen undergoes alkaline and acidic hydrolysis, respectively, and forms baclofen-related Compound A which is listed in the USP monograph as a known impurity (BRC A) that must be controlled to within certain limits.

Preparation of a stable baclofen oral solution at near neutral pH at a concentration of about 5 mg/mL or more remains a critical challenge, because baclofen is not soluble at a concentration of 2 mg/mL in near neutral pH. Moreover, an increase or decrease in pH of the oral solution leads to formation of impurities.

Various sources have reported stable suspensions or syrups of baclofen for oral administration that had concentrations higher than an equilibrium concentration of 4.3 mg/mL (Allen et al., 1996; Johnson and Hart, 1993), but none of these preparations were acceptable for pharmaceutical uses.

U.S. Pat. No. 8,357,379 discloses aqueous solutions comprising baclofen in concentrations greater than 2 mg/mL up to about 10 mg/mL. These solutions were prepared by heat and sonication; high speed stirring; alkalization with back titration; acidification with back titration. U.S. Pat. No. 9,655,968 discloses aqueous solutions comprising baclofen in multivalent physiological ion solution such as artificial cerebrospinal fluid at concentrations of 10 mg/mL. The aqueous solutions disclosed in the above patents contains normal saline or multivalent physiological ion solution as solvents which are preferred diluents for injectable dosage forms and not preferred for preparing oral dosage forms.

What is needed is a method for providing a high-concentration, stable liquid pharmaceutical compositions of baclofen for oral administration, without requiring use of strong acids or strong bases for dissolving baclofen, and without utilizing sonication and intense agitation to dissolve the baclofen. There also appears to be a clinical need for providing concentrated aqueous solutions of baclofen for oral administration, having acceptable pharmaceutical properties, and most preferably, concentrated solutions that are stable in a variety of storage conditions and for extended periods of time.

Furthermore, baclofen undergoes acidic and basic hydrolysis at very high or very low pH ranges. Therefore, there remains a need to develop a liquid pharmaceutical composition of baclofen for oral administration which is stable at pH ranges of about 5-8.

SUMMARY OF THE INVENTION

In one aspect, liquid pharmaceutical compositions for oral administration are provided, which comprise baclofen, a pharmaceutically acceptable excipient, and at least one pharmaceutically acceptable liquid vehicle, wherein baclofen is present at a concentration of about 2 mg/mL or more, and wherein the liquid pharmaceutical composition is stable. Preferably, a pharmaceutical composition may comprise: (i) about 5 mg/mL of baclofen; (ii) about 50 mg/mL of cyclodextrin or cyclodextrin derivative; (iii) about 2 mg/mL preservative; (iv) at least one pharmaceutically acceptable liquid vehicle; (v) a flavouring agent; and (vi) a sweetener.

In another aspect, a process for the preparation of a stable, liquid pharmaceutical formulation for oral administration comprising baclofen is provided, where the process comprising the steps of: (a) heating a pharmaceutically acceptable excipient (e.g., water) to a temperature of up to about 60° C.; (b) adding cyclodextrin or cyclodextrin derivative to the water to form a first solution; (c) stirring the first solution to obtain a first clear solution; (d) adding baclofen to the first clear solution to form a second solution; (e) stirring the second solution to obtain a second clear solution; (f) optionally, adding at least one other pharmaceutically acceptable excipient; and (g) stirring to obtain a final clear solution.

Another aspect relates to methods of treatment using the pharmaceutical compositions. Specifically provided is a method for managing or treating or alleviating the signs and symptoms of spasticity resulting from multiple sclerosis or spinal cord damage or spinal cord disease in a patient by orally administering an effective amount of a liquid pharmaceutical composition, according to the invention, to an adult, pediatric or geriatric patient.

Each aspect above may further have one or more of the following additional elements in any combination:

Element 1: wherein baclofen is present at a concentration from about 5 mg/mL to about 10 mg/m L.

Element 2: wherein the pharmaceutical composition is selected from the group consisting of an aqueous solution, a syrup and an elixir.

Element 3: wherein the pharmaceutically acceptable excipient is selected from the group consisting of a solubilizer, a sweetening agent, a flavoring agent, a preservative, an antioxidant, a viscosity modifier, a pH adjusting agent, a buffering agent, a coloring agent, a surfactant and mixtures thereof.

Element 4: wherein the solubilizer is selected from the group consisting of cyclodextrin, cyclodextrin derivatives and mixtures thereof. The cyclodextrin or cyclodextrin derivative may be selected from the group consisting of α-cyclodextrin, β-cyclodextrin, δ-cyclodextrin, γ-cyclodextrin, and combinations thereof. Preferably, the cyclodextrin or cyclodextrin derivative is selected from the group consisting of hydroxypropyl-β-cyclodextrin (HP-β-CD), methyl-β-cyclodextrin, sulfobutylether-β-cyclodextrin (SBE-β-CD), hydroxypropyl-γ-cyclodextrin and combinations thereof.

Element 5: wherein the cyclodextrin or cyclodextrin derivative is present at a concentration of about 10 mg/mL to about 400 mg/mL, preferably from about 25 mg/mL to about 100 mg/mL, more preferably about 50 mg/mL.

Element 6: wherein the cyclodextrin or cyclodextrin derivative is present at a concentration of about 10 mg/mL to about 400 mg/mL, preferably from about 25 mg/mL to about 100 mg/mL, more preferably about 50 mg/mL.

Element 7: wherein the weight ratio of cyclodextrin or cyclodextrin derivative to baclofen is from about 1:1 to about 80:1, preferably from about 5:1 to about 20:1, more preferably about 10:1.

Element 8: wherein the weight ratio of cyclodextrin or cyclodextrin derivative to baclofen is from about 1:1 to about 80:1, preferably from about 5:1 to about 20:1, more preferably about 10:1.

Element 9: wherein the liquid pharmaceutical composition has a pH in the range of about 5 to about 8, preferably between about 6 to about 7.

Element 10: wherein the composition is stable for at least 6 months at 40° C./75% RH.

Element 11: wherein the composition is stable for at least 12 months at about 2° C. to 8° C.

Element 12: wherein the level of BRC A Impurity in the composition is less than about 2% (w/w), preferably less than about 1.5% (w/w), more preferably less than about 1% (w/w) as measured by HPLC.

By way of non-limiting example, exemplary combinations applicable to the embodiments described in this application may include any combination with one or more of Elements 1-12, described above.

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail.

As used herein the term "baclofen" refers to baclofen free base or a pharmaceutically acceptable salt, solvate or hydrate thereof. It also includes geometric isomer or a stereoisomer thereof. In certain aspects, baclofen free base may be used. Any crystalline form of baclofen as well as the amorphous form may be used for the preparation of pharmaceutical compositions of the present invention.

The terms "pharmaceutical composition," "pharmaceutical product," "pharmaceutical dosage form," "dosage form," "pharmaceutical formulation," etc., refer to a pharmaceutical composition that may be administered to a patient in need of treatment, which may be in any conventional formulation. For example, the term "pharmaceutical composition" as used herein includes an aqueous solution, a syrup or an elixir.

Within the context of this invention, the term "solution" refers to a mixture of one or more substances dispersed molecularly (i.e., dissolved) in a dissolving liquid medium or vehicle. The solution is preferably homogeneous, in the sense that each API is essentially uniformly distributed and concentrated in the solution. The liquid solution may be viscous (such as syrup) or not. As already mentioned, a liquid solution differs from a suspension which comprises solid particles dispersed throughout a liquid phase in which they are not soluble.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or color. The term "Stable" indicates both chemical and physical stability.

The present application relates to stable liquid pharmaceutical compositions of baclofen or its pharmaceutically acceptable salt or ester thereof, particularly wherein baclofen is present at a concentration of 2 mg/mL or more. In one aspect, a pharmaceutical composition of the present application comprises baclofen or a pharmaceutically acceptable salt thereof, wherein baclofen concentration is about 2 mg/mL to about 20 mg/mL and preferably 5 mg/mL or more.

In certain aspects, the pharmaceutical compositions of the present application increase solubility of baclofen by one or more of methods selected from (a) particle size reduction, (b) solid dispersion, (c) complexation using a solubility enhancer (d) high speed stirring.

The present application also provides pharmaceutical composition comprising baclofen or its pharmaceutically acceptable salts thereof and a solubilizer. In certain aspects, the solubilizer may be selected from the group consisting of cyclodextrin, cyclodextrin derivative, HPMC, poloxamer 188, glycerine, polysorbate 80, PEG 400 and combinations thereof. In another aspect, the pharmaceutical composition of the present application comprises baclofen or its pharmaceutically acceptable salts thereof and a solubilizer, wherein the composition further comprises additional pharmaceutically acceptable excipients.

In yet another embodiment, the present application provides pharmaceutical composition comprising baclofen or its pharmaceutically acceptable salts thereof and solubilizer, wherein the solubilizer is a buffering agent. In another embodiment, pharmaceutical composition of the present application comprises baclofen and cyclodextrin or a cyclodextrin derivative as solubilizer.

In one preferred aspect, the invention relates to liquid pharmaceutical compositions comprising baclofen or its pharmaceutically acceptable salts thereof and cyclodextrin or a cyclodextrin derivative for oral administration. The pharmaceutical composition comprises baclofen and a cyclodextrin derivative, wherein baclofen concentration is from about 2 mg/mL to about 20 mg/mL, preferably about 5 mg/mL. In another aspect, a pharmaceutical composition according to the invention comprises baclofen and a cyclodextrin derivative, wherein the concentration of cyclodextrin derivative is from about 10 mg/mL to about 400 mg/mL, preferably from about 25 mg/mL to about 100 mg/mL, most preferably about 50 mg/mL. According to another aspect, the pharmaceutical composition of the present application comprises baclofen and a cyclodextrin derivative, wherein the composition further comprises additional pharmaceutically acceptable excipients.

In one embodiment, pharmaceutical composition comprising baclofen can be formulated at any suitable pH. The pH of the pharmaceutical composition is preferably from about 5 to about 8, when measured at room temperature. In one embodiment, pharmaceutical composition comprising baclofen can be formulated by using any suitable pH adjusting agent. In a preferred aspect, it is possible to maintain the pH of the said composition without using a suitable buffering agent.

In yet another embodiment, the present application relates to method of treating signs and symptoms of spasticity in a subject, the method comprising administering the subject a pharmaceutical composition comprising baclofen and a cyclodextrin derivative for oral administration.

In yet further embodiment, the present application relates to method of treating spasticity resulting from multiple sclerosis, particularly for the relief of flexor spasms and concomitant pain, clonus, and muscular rigidity and spasticity due to spinal cord diseases or damage by oral administering the pharmaceutical composition comprising baclofen and a cyclodextrin derivative.

Preferably, the liquid pharmaceutical composition will be provided in a dosage form that is suitable for oral administration, including but not limited to a solution, syrup, or elixir. The pharmaceutical compositions may be formulated according to conventional pharmaceutical practice.

As used herein "aqueous solution" means a solution that is at least 80% water by weight, preferably at least 90% water by weight, more preferably at least 95% water by weight and most preferably at least 98% water by weight. In certain embodiments, aqueous solutions of the present invention include solutions containing appropriate buffering agents, preservatives, other pharmaceutically acceptable additives or any combination thereof. Alternately, aqueous solutions of the present invention can contain no such additives and can consist solely of baclofen, a pharmaceutically acceptable solubilizer, and water.

Generally, the present invention provides stable aqueous baclofen solutions at concentrations higher than the 2.0 mg/mL concentration, and methods of preparing such solutions. In particular, the present invention provides stable aqueous baclofen solutions for oral administration having concentrations greater than about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 and 6.0 mg/mL. The present invention provides stable aqueous baclofen solutions having concentrations less than about 4.0, 4.5, 5.0, 5.5, 6.0, 6.5, 7.0, 7.5, 8.0, 8.5, 9.0, 9.5, 10.0, 10.5, 11.0, 11.5 or 12.0 mg/mL.

In an embodiment, pharmaceutical composition comprising baclofen, has a concentration of about 2 mg/mL, about 3 mg/mL, about 4 mg/mL, about 5 mg/mL, about 6 mg/mL, about 7 mg/mL, about 8 mg/mL, about 9 mg/mL, 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, and 20 mg/mL, most preferably about 5 mg/mL.

In an embodiment, one or more pharmaceutically acceptable excipients combined with baclofen comprises solubilizers, sweetening agents, flavoring agents, preservatives, antioxidants, viscosity modifiers, pH adjusting agents, buffering agents, coloring agents, surfactants and combinations thereof.

In one aspect, the present application provides pharmaceutical composition comprising baclofen or its pharmaceutically acceptable salts thereof and a solubilizer. In another aspect, the pharmaceutical composition of the present application comprises baclofen or its pharmaceutically acceptable salts thereof and a solubilizer, where in the composition further comprises additional pharmaceutically acceptable excipients. In an embodiment, suitable solubilizers include cyclodextrins, cyclodextrin derivatives, hydroxypropylmethyl cellulose, glycerol, polyethylene glycol, poloxamer and polysorbate.

In another embodiment, pharmaceutical composition of the present application comprises baclofen and a solubilizer, wherein concentration of the solubilizer is from about 10 mg/mL to about 400 mg/mL.

In another embodiment, pharmaceutical composition of the present invention comprises baclofen and a solubilizer, wherein concentration of the solubilizer is from about from about 25 mg/mL to about 100 mg/mL, preferably about 50 mg/mL In another embodiment, pharmaceutical composition of the present application comprises baclofen and a cyclodextrin or cyclodextrin derivative, where in the composition further comprises additional pharmaceutically acceptable excipients.

The present application relates to pharmaceutical compositions comprising baclofen or its pharmaceutically acceptable salts thereof and a cyclodextrin derivative.

In another embodiment, pharmaceutical composition of the present application comprises baclofen and a cyclodextrin derivative, wherein cyclodextrin derivative concentration is about 10 mg/mL to about 400 mg/mL, preferably from about 25 mg/mL to about 100 mg/mL, more preferably about 50 mg/mL In one embodiment, the cyclodextrin of the present application includes α-cyclodextrin, β-cyclodextrin, δ-cyclodextrin, γ-cyclodextrin, or combinations thereof. In an embodiment, the cyclodextrin of the present application preferably includes either a substituted or non-substituted β-cyclodextrin.

Substituted cyclodextrins increase the solubility of the cyclodextrin and mitigate toxic effects associated with unsubstituted cyclodextrins. Examples of substituted β-cyclodextrins include those substituted with one or more hydrophilic groups, such as monosaccharide (e.g., glucosyl, maltosyl), carboxyalkyl (e.g., carboxyl methyl, carboxyethyl), hydroxyalkyl-substituted (e.g., hydroxyethyl, 2-hydroxypropyl) and sulfoalkylether-substituted-β-cyclodextrin.

In one embodiment, the cyclodextrin is a substituted β-cyclodextrin, particularly, hydroxypropyl-β-cyclodextrin (HP-β-CD) and sulfobutylether-β-cyclodextrin (SBE-β-CD). However, it is understood that typically any substitution to the cyclodextrin, including substitution by hydrophobic groups such as hydroxyalkyl-substituted-cyclodextrin, will improve its aqueous solubility by disrupting the hydrogen-bonding network within the crystal lattice of the solid cyclodextrin, thereby lowering the lattice energy of the solid. The degree of substitution is not believed to be critical; however, the degree of substitution is advantageously at least 1% and typically 2% to 10%, such as 3% to 6%.

In a preferred embodiment, the cyclodextrin derivative is a substituted β-cyclodextrin, particularly suitable β-cyclodextrins include for example but not limited to, Cavasol® W7 HP (hydroxypropyl-β-cyclodextrin (HP-β-CD), Kleptose® HP (hydroxypropyl-β-cyclodextrin (HP-β-CD)), Cavamax® W7 (β-cyclodextrin), Captisol® (sulfoalkyl ether-β-cyclodextrin), Cavasol® W7 M (methyl-β-cyclodextrin), Cavasol® W8 HP (hydroxypropyl-γ-cyclodextrin), Cavamax® W8 (γ-cyclodextrin), Cavamax® W6 (α-cyclodextrin).

In one aspect, the cyclodextrin is 2-hydroxypropyl-β-cyclodextrin (HP-β-CD), which is a cyclic oligosaccharide containing seven D-(+)-glucopyranose units.

In an embodiment, pharmaceutical compositions comprising baclofen, wherein the weight ratio of cyclodextrin or cyclodextrin derivative to baclofen is from about 1:1 to about 80:1, preferably from about 2:1, about 3:1, about 4:1, about 5:1, about 6:1, about 7:1, about 8:1, about 9:1, about 10:1, about 11:1 and to about 12:1.

In another embodiment, pharmaceutical compositions comprising baclofen, wherein the weight ratio of cyclodextrin or cyclodextrin derivative to baclofen is from about 1:1 to about 80:1, preferably from about 10:1 to about 40:1 and more preferably about 20:1.

In further embodiment, pharmaceutical compositions comprising baclofen, wherein the weight ratio of cyclodextrin or cyclodextrin derivative to baclofen is from about 1:1 to about 40:1, preferably from about 5:1 to about 20:1, more preferably about 10:1.

In compositions of the invention, HP-β-CD may form an inclusion complex with baclofen and increase its solubility to greater than 2 mg/mL, whilst at the same time, forming a stable oral solution suitable for long term storage under different storage conditions.

In an embodiment, pharmaceutical composition comprising baclofen can be formulated at any suitable pH. As noted above, at very high or very low pH values, baclofen undergoes hydrolysis resulting in increased impurity formation. Preferably, pH of pharmaceutical composition can be from about 5 to about 8 when measured at room temperature. Preferably, the pH is about 7.

In an embodiment, the invention relates to stable aqueous solutions of baclofen intended for oral administration comprising baclofen at a concentration of about 5 mg/mL and a buffer, wherein the solution has a pH in between 3-5, and wherein the solution is stable for at least 6 months at 2° C.-8° C.

In an embodiment, the invention relates to stable aqueous solutions of baclofen intended for oral administration comprising baclofen at a concentration of about 5 mg/mL and a buffer, wherein the solution has a pH in between 3-5, and wherein the solution is stable for at least 6 months at 25° C./60% RH.

In an embodiment, pharmaceutical composition comprising baclofen can be formulated at any suitable pH using pH adjusting agent and to maintain pH of the said composition using suitable buffering agent.

In an embodiment, suitable pH adjusting agent include acetic acid, ammonia solution, strong; acetic acid, glacial; ammonium carbonate; citric acid, anhydrous; diethanolamine; citric acid monohydrate; potassium hydroxide; fumaric acid; sodium bicarbonate; hydrochloric acid; sodium borate; hydrochloric acid, diluted; sodium carbonate; malic acid; trolamine; phosphoric acid; sodium hydroxide; nitric acid; phosphoric acid, diluted; propionic acid; sulfuric acid; tartaric acid.

In an embodiment, suitable buffering agents include acetic acid; adipic acid; ammonium carbonate; ammonium phosphate; boric acid; citric acid anhydrous; citric acid monohydrate; lactic acid; phosphoric acid; potassium citrate; potassium metaphosphate; potassium phosphate, dibasic; potassium phosphate, monobasic; sodium acetate; sodium citrate; sodium lactate solution; sodium phosphate, dibasic; sodium phosphate, monobasic; succinic acid.

In an embodiment, suitable sweetening or flavoring agents include aspartame, sucralose, and the like and/or cherry flavor, artificial banana flavor, caramel, chocolate mint flavor, grape flavor, wild cherry flavor, raspberry flavor, strawberry flavor, mixed berry flavor, citrus flavor, orange flavor, pineapple flavor, citrus lime flavor, citrus cream flavor, cherry vanilla flavor, creme de menthe flavor and mixtures thereof.

In an embodiment, suitable viscosity modifiers include cellulose or cellulose derivatives such as ethylcellulose, hydroxyethylcellulose, hydroxypropylcellulose, caboxymethylcellulose, sodium hydroxypropyl methylcellulose, hypromellose, methylcellulose, methylethylcellulose, sodium carboxymethylcellulose, Aerosil (silicon dioxide), cetostearyl alcohol, cetyl alcohol, stearyl alcohol, Gelucires 33/01, 39/01 and 43/01, stearyl alcohol carbomer, xanthan gum, maltodextrin, acacia, tragacanth, povidone and polyvinyl alcohol and mixtures thereof.

In an embodiment, suitable preservatives include antimicrobials, antioxidants, and agents that enhance sterility. Exemplary preservatives include ascorbic acid, ascorbyl palmitate, benzyl alcohol, xylitol, butylated hydroxyanisole (BHA), butylated hydroxytoluene (BHT), citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, butyl-), benzoic acid, potassium sorbate, and vanillin.

In an embodiment, pharmaceutical composition of the present application comprises baclofen, solubilizer and a preservative, wherein concentration of the preservative is from about from about 0.1 mg/mL to about 10 mg/mL, preferably about 5 mg/mL In an embodiment, pharmaceutical composition of the present application comprises baclofen, cyclodextrin or cyclodextrin derivative and a preservative, wherein concentration of the preservative is from about from about 0.1 mg/mL to about 5 mg/mL, preferably about 2 mg/mL.

Any appropriate form of baclofen can be used to prepare oral solutions of the present invention. For example, any crystalline or amorphous form of baclofen may be used in the pharmaceutical composition of the present application. In preferred embodiments, appropriate forms of baclofen include baclofen solids such as powdered, lyophilized, spray-dried, hot-melt extruded or microfluidized baclofen. In other embodiments, the baclofen can be provided as an aqueous or non-aqueous solution of baclofen, including buffered solutions.

In an embodiment, pharmaceutical compositions of the present application increase solubility of baclofen by one or more of methods selected from (a) particle size reduction, (b) solid dispersion, (c) complexation (d) high speed stirring.

In an embodiment, a process for preparing pharmaceutical compositions of the present invention involves a heating and stirring method comprises: (a) heating a solvent up to about 60° C., (b) adding a solubilizer (e.g., a cyclodextrin or a derivative thereof) and stirring until a clear solution is observed, followed by adding baclofen and continued stirring until a clear solution is observed; (c) allowing the solution from (b) to cool until the temperature reaches room temperature; (d) optionally, adding any other pharmaceutically acceptable excipient(s) and stirring until a clear solution is observed; and (e) finally making up the volume of solution to the desired solution concentration and filling in a suitable pharmaceutically acceptable container(s).

The pharmaceutical compositions of present application may be filled into any suitable pharmaceutically acceptable containers. For example, the pharmaceutically acceptable container may be selected from group consisting of bottles and syringes.

The bottle can be made of any material convenient with the storage and the use requirements comprising polymers, metal and glass and so on. It is of importance that the bottle material does not interfere with the components of the liquid formulation as disclosed herein. In an embodiment it is made of glass. In order to protect the APIs from light-induced degradation, a preferred embodiment comprises amber glass bottle.

The bottle capacity can be adapted to the volume to be administrated for the period during which the liquid formulation as disclosed herein is stable. For instance, a solution which is stable for 10 days after opening associated to an administration of two doses of 5 mL per day may be stored into bottle of about 100 mL. The one skilled in the art will easily adapt the volume of the bottle to that needed as previously suggested.

The pipette is made of glass, plastic or any material convenient with the use and the storage of the liquid solutions as disclosed herein. The pipette may be graduated to facilitate the administration of the liquid solution. In an embodiment, the pipette is a 5 mL graduated pipette.

The cap (or closure) is any article for closing a suitably shaped opening. It encompasses, but is not limited to, childproof closures, waterproof closures, pipette-associated caps, solid caps, plastic or polymeric caps. In an embodiment, the cap is screwed on the bottle top or interlocked with the top of the bottle.

A sealing element may be required for the tightness of the system bottle-cap or bottle-pipette-cap or bottle-pipette or pipette-cap. This element can be supplied on its own and further fit in the bottle-neck, or around the pipette, or in the cap, or it can be previously adapted to the bottle, the cap or the pipette.

The invention also relates to a kit of parts comprising a package containing bottles of the liquid formulation as disclosed herein and pipettes intended to remove the needed amount of the liquid formulation and/or instructions.

In another aspect, the invention relates to a kit of parts allowing the extemporaneously preparation of the solutions according to the invention.

In an embodiment, the pharmaceutically acceptable container may be a bottle, wherein the bottle was selected from group consisting of a glass bottle and a plastic bottle. Examples of glass bottle include, but are not limited to Type I, II and III borosilicate glass bottles. In an embodiment, the pharmaceutically acceptable container was a glass bottle, wherein the glass bottle may be amber colour glass bottle or clear glass bottle. Examples of plastic bottles include, but are not limited to, high-density polyethylene (HDPE), polyethylene terephthalate (PET) and polypropylene (PP) bottles. In an embodiment, the pharmaceutically acceptable container is a plastic bottle, wherein the plastic bottle may be amber colour, white opaque or translucent plastic bottle. In preferred embodiment, the HDPE bottles will be available in 30, 60, 120, 250 & 500 ml fill volumes.

In an embodiment, the pharmaceutical composition of present application was packed in a kit comprising bottle with child resistant cap, dosing syringe, adapter and dosing syringe.

Stability

As used herein, the term "stable" is defined as no more than about 5% loss of baclofen under typical commercial storage conditions. In certain embodiments, the formulations of the present invention will have no more than about 3% loss of baclofen, more preferably, no more than about 2% loss of baclofen, under typical commercial storage conditions. The composition retains at least about 95% of the potency of baclofen after storing the composition at 40° C. and 75% relative humidity for at least three months. In certain aspects, the term "stable" refers to chemical stability, wherein not more than 1.5% w/w of total related substances are formed on storage at accelerated conditions of stability at 40° C. and 75% relative humidity or at 25° C. and 60% relative humidity or 2-8° C. for a period of at least six months or to the extent necessary for use of the composition.

In particular, the BRC A Impurity (i.e., 4-(4-Chlorophenyl)-2-pyrrolidinone) may be monitored. The structure of BRC A Impurity is shown below:

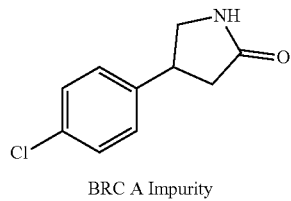 [SMILES: O=C1CC(c2ccc(Cl)cc2)CN1]

BRC A Impurity

Compositions of the present application were found to remain in solution, without any recrystallization or precipitation, when stored for 6 months at 2-8° C., 25° C./60% relative humidity (RH) condition or 40° C./75% relative humidity (RH) conditions.

In an embodiment, the pharmaceutical compositions of the present application were subjected to freeze-thaw cycle testing to determine stability, phase separation or precipitation or crystallization under high and low temperature conditions.

Freeze-thaw testing is conducted by exposing the product to freezing temperatures (2 to 8° C.) for at least 24 hours, and then allowing it to thaw at 40° C. and 75% RH for at least 24 hours. This process is referred to as one Freeze-thaw cycle. Samples were subjected from 1 to 7 Freeze-thaw cycles. The sample was analysed visually for particles or crystals.

In an embodiment, the invention relates to stable aqueous solutions of baclofen intended for oral administration comprising about 5 mg/mL baclofen and Hydroxypropyl-β-cyclodextrin (HP-β-CD), wherein the solution is stable for at least 6 months at 40° C./75% relative humidity (RH) condition.

In another embodiment, the invention relates to stable aqueous solutions of baclofen intended for oral administration comprising about 5 mg/mL baclofen and Hydroxypropyl-β-cyclodextrin (HP-β-CD), wherein the solution is stable for at least 3 months at 2° C.-8° C.

In another embodiment, the invention relates to stable aqueous solutions of baclofen intended for oral administration comprising about 5 mg/mL baclofen and Hydroxypropyl-β-cyclodextrin (HP-β-CD), wherein the solution is stable for at least 12 months at about 2° C.-8° C.

In another embodiment, the invention relates to stable aqueous solutions of baclofen intended for oral administration comprising about 5 mg/mL baclofen and Hydroxypropyl-β-cyclodextrin (HP-β-CD), wherein the solution is stable for at least 6 months at 25° C./60% relative humidity (RH) condition.

In yet another embodiment, the invention relates to stable aqueous solutions of baclofen intended for oral administration comprising about 5 mg/mL baclofen and Hydroxypropyl-β-cyclodextrin (HP-β-CD), wherein the solution when stored for at least 6 months at 40° C./75% relative humidity (RH) condition exhibits less than about 2% (w/w), preferably less than 1.5% (w/w), more preferably less than 1% (w/w) of BRC A Impurity as measured by HPLC.

In another embodiment, the invention relates to stable aqueous solutions of baclofen intended for oral administration comprising about 5 mg/mL baclofen and Hydroxypropyl-β-cyclodextrin (HP-β-CD), wherein the solution when stored for at least 3 months at 2° C.-8° C. exhibits less than about 1% (w/w) of BRC A Impurity as measured by HPLC.

In another embodiment, the invention relates to stable aqueous solutions of baclofen intended for oral administration comprising about 5 mg/mL baclofen and Hydroxypropyl-β-cyclodextrin (HP-β-CD), wherein the solution when stored for at least 6 months at 2° C.-8° C. exhibits less than about 1% (w/w) of BRC A impurity as measured by HPLC.

In another embodiment, the invention relates to stable aqueous solutions of baclofen intended for oral administration comprising about 5 mg/mL baclofen and Hydroxypropyl-β-cyclodextrin (HP-β-CD), wherein the solution when stored for at least 12 months at 2° C.-8° C. exhibits less than about 2% (w/w), preferably less than 1.5% (w/w), more preferably less than about 1% (w/w) of BRC A impurity as measured by HPLC.

In an embodiment, the invention relates to stable aqueous solutions of baclofen intended for oral administration comprising about 5 mg/mL baclofen and Hydroxypropyl-β-cyclodextrin (HP-β-CD), wherein the solution further optionally comprises sweetening agents, preservatives and flavoring agents, and wherein pH of the aqueous solution is in between 5-8.

In an embodiment, the invention relates to stable aqueous solutions of baclofen intended for oral administration comprising about 5 mg/mL baclofen and Hydroxypropyl-β-cyclodextrin (HP-β-CD), wherein the solution further comprises sucralose as sweetening agent, and wherein pH of the aqueous solution is in between 5-8.

In an embodiment, the invention relates to stable aqueous solutions of baclofen intended for oral administration comprising about 5 mg/mL baclofen and Hydroxypropyl-β-cyclodextrin (HP-β-CD), wherein the solution further comprises sucralose as sweetening agent, methyl paraben and propyl paraben as preservatives, and wherein pH of the aqueous solution is in between 5-8.

In an embodiment, the invention relates to stable aqueous solutions of baclofen intended for oral administration, comprising about 5 mg/mL baclofen, about 50 mg/mL of cyclodextrin or a cyclodextrin derivative; about 2 mg/mL of preservative; a flavouring agent; and a sweetener.

In an embodiment, the invention relates to stable aqueous solutions of baclofen intended for oral administration comprising 5 mg/mL baclofen, about 50 mg/mL of cyclodextrin or cyclodextrin derivative; about 2 mg/mL preservative, and optionally a flavouring agent, and a sweetener.

In an embodiment, the invention relates to stable aqueous solutions of baclofen intended for oral administration comprising 5 mg/mL baclofen, about 50 mg/mL of cyclodextrin or cyclodextrin derivative; about 2 mg/mL preservative, and optionally a flavouring agent, and a sweetener, wherein pH of the aqueous solution is in between about 5-8.

Dosage and Administration

The pharmaceutical compositions as described herein may be used in methods of treatment, in which an effective amount of baclofen or a pharmaceutically acceptable salt thereof is administered to a patient.

For administration to animal or human subjects, the pharmaceutical compositions comprise an effective dosage amount of baclofen or a pharmaceutically acceptable salt thereof. The formulation may be prepared using conventional methods, for example, depending on the subject to be treated, the mode of administration, and the type of treatment desired (e.g., prevention, prophylaxis, or therapy).

Preferably, the present application relates to method for managing or treating or alleviating signs and symptoms of spasticity resulting from multiple sclerosis in a subject, the method comprising administering the subject a pharmaceutical composition comprising baclofen or its pharmaceutically acceptable salts thereof and a cyclodextrin derivative or a solubilizer.

In other aspect, the present application relates to method for managing or treating or alleviating the signs and symptoms of spasticity resulting from multiple sclerosis or spinal cord damage or spinal cord disease in the subject, wherein the method comprising administering the subject a pharmaceutical composition comprising baclofen or its pharmaceutically acceptable salts thereof and a cyclodextrin derivative or a solubilizer.

In one aspect, the present application relates to method of treating signs and symptoms of spasticity resulting from multiple sclerosis, spinal cord disease or spinal cord damage in a subject by administering a pharmaceutical composition comprising baclofen or its pharmaceutically acceptable salts thereof and a cyclodextrin derivative or solubilizer, wherein particularly for the relief of flexor spasms and concomitant pain, clonus, and muscular rigidity.

Determination of baclofen optimal dosage may require individual titration. Therapy may be started at a low dosage, and increase gradually until optimum effect is achieved (e.g., usually between 40-80 mg daily). In certain embodiments, 1-50 mL of baclofen oral solution may be administered to achieve optimum effect, preferably 3-20 mL may be administered to achieve optimum effect.

In an embodiment, the present application relates to method of treating signs and symptoms of spasticity resulting from multiple sclerosis in adult patient, the method comprising administering 5 mg three times a day for 3 days or 10 mg three times a day for 3 days or 15 mg three times a day for 3 days or 20 mg three times a day for 3 days or additional increases may be necessary up to the maximum recommended dosage of 80 mg daily (20 mg four times a day) to the subject a pharmaceutical composition comprising baclofen or its pharmaceutically acceptable salts thereof and a cyclodextrin derivative or solubilizer.

In an embodiment, the present application relates to method of treating signs and symptoms of spasticity resulting from multiple sclerosis in patients of age less than 18 years with dose from 0.3 mg/kg a day to 2.5 mg/kg a day, in 2 to 4 divided doses to the subject a pharmaceutical composition comprising baclofen or its pharmaceutically acceptable salts thereof and a cyclodextrin derivative or solubilizer.

In certain aspects, the pharmaceutical compositions described herein may be used to treat adults and adolescents (e.g., about 13-17 years). In certain aspects, the pharmaceutical compositions described herein may be used as monotherapy or as adjunctive therapy. For example, additional active agents may be used in adjunctive therapy with baclofen, such as pain medications (e.g., morphine, hydromorphone, etc.).

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

By "effective" amount is meant the amount of a drug sufficient to treat, prevent, or ameliorate a condition in a subject or patient. The effective amount of baclofen or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

General HPLC Procedure

As explained in detail below, the following HPLC procedure can be used to detect and quantify impurities of Baclofen as well as assay calculation. The materials and general conditions are listed below:

Chromatographic Conditions

TABLE 1

| Column | Prime Sep 100 A°, 150 × 4.6 mm, 5µ (Part No.: 100.46.150.510) |
|---|---|
| Column Temperature | 40° C. |
| Flow rate | 1.0 mL/min |
| Detector | 220 nm with PDA/UV detector |
| Injection volume | 20 µL |
| Run time | 60 min |
| Mobile Phase A | 1 mL of methane sulfonic acid in 1000 mL of water |
| Mobile Phase B | mixture of acetonitrile and water in 90:10% v/v ratio |

Gradient Program

TABLE 2

| Time (min) | % A | % B |
|---|---|---|
| 0.01 | 90 | 10 |
| 40 | 60 | 40 |
| 50 | 50 | 50 |
| 52 | 90 | 10 |
| 60 | 90 | 10 |

Example 1

TABLE 3

| | Composition | | |
|---|---|---|---|
| | A | B | C |
| Ingredients | Quantity/batch | | |
| Baclofen | 250 mg | 250 mg | 250 mg |
| HP-β-CD | 500 mg | 1500 mg | 2500 mg |
| Purified Water | q.s. to 50 mL | q.s. to 50 mL | q.s. to 50 mL |

About 45 mL of the purified water was heated to 55-65° C. in a manufacturing vessel. Specified amount of HP-β-CD was added to the water at 55-65° C. and stirred for 5-10 minutes to obtain clear solution. Baclofen was added to the obtained solution and continued stirring for another 15-minutes at 55-65° C. Remaining amount of water was added to make up the solution to 50 mL and allowed to cool to room temperature.

Samples of Composition A, B and C were stored for 30 days at 25° C./60% RH condition as well as 40° C./75% RH conditions, baclofen remains solubilized and compositions were found to be clear without any recrystallization or precipitation.

These compositions were also subjected to freeze thaw cycling and observed for any visible particles or crystals by physical observation. No visible particles or crystal particles were observed in composition B and C after 7 cycles of Freeze-thaw. Crystals observed in Composition A after 2 cycles of Freeze-thaw.

Further Composition C was stored at 2° C.-8° C. for at least 3 months and at 40° C./75% RH for 6 months.

TABLE 4

| | Composition C | |
|---|---|---|
| Condition | 2-8° C. | 40°C./75% RH |
| Duration | 3 Months | 6 Months |
| Pack | HDPE | HDPE |
| Visual observation | Clear solution | Clear solution |
| Impurity Profile | | |
| BRC A (Known Impurity) | ND | 0.68 |
| Unknown impurity | ND | 0.39 |
| Total impurity | ND | 1.07 |

The Composition C is both physically and chemically stable for longer duration of time, without visible particles and no significant increase in the total known (BRC A) and unknown impurities.

Example 2

TABLE 5

| | Composition | | | | |
|---|---|---|---|---|---|
| | D | E | F | G | H |
| Ingredients | Quantity/batch | | | | |
| Baclofen | 250 mg | 250 mg | 250 mg | 250 mg | 250 mg |
| HP-β-CD | 500 mg | 1500 mg | 2500 mg | 500 mg | 2500 mg |
| HPMC (5 cps) | 50 mg | 50 mg | 50 mg | 250 mg | 250 mg |
| Purified Water | q.s. to 50 mL | q.s. to 50 mL | q.s. to 50 mL | q.s. to 50 mL | q.s. to 50 mL |

About 40 mL of the purified water was heated to 55-65° C. in a manufacturing vessel. Specified amount of HP-β-CD was added to the water at 55-65° C. and stirred for 5-10 minutes to obtain clear solution. Baclofen was added to the obtained solution and continued stirring for another 15-minutes at 55-65° C. The resultant solution was allowed to cool to room temperature.

Required amount of HPMC was dissolved in 8 mL of water at 25-35° C. and added to the Baclofen solution under stirring to get clear solution. Remaining amount of water was added to make up the solution to 50 mL.

Samples of Composition D, E, F, G and H were stored for 30 days at 25° C./60% RH condition as well as 40° C./75% RH conditions, baclofen remains solubilized and compositions are clear without any recrystallization or precipitation.

These compositions were also subjected to freeze thaw cycling and observed for any visible particles or crystals by physical observation. No visible particles of Baclofen were observed after 6 Freeze-Thaw cycles in Composition E, F and H. Visible particles were observed after 2 Freeze-Thaw cycles in Composition D and G.

Example 3

TABLE 6

| Ingredients | Composition I | J | K | L |
|---|---|---|---|---|
| | Quantity/batch | | | |
| Baclofen | 250 mg | 250 mg | 250 mg | 250 mg |
| Glycerine | 1000 mg | — | — | — |
| Poloxamer 188 | — | 1500 mg | — | — |
| Polysorbate 80 | — | — | 1000 mg | — |
| PEG 400 | — | — | — | 1500 mg |
| Purified Water | q.s. to 50 mL | q.s. to 50 mL | q.s. to 50 mL | q.s. to 50 mL |

About 45 mL of the purified water was heated to 55-65° C. in a manufacturing vessel. Specified amount of solubilizing agent was added to the water at 55-65° C. and stirred for 5-10 minutes to obtain clear solution. Baclofen was added to the obtained solution and continued stirring for another 15-30 minutes at 55-65° C. Remaining amount of water was added to make up the solution to 50 mL and allowed to cool to ambient temperature.

Samples of Composition I, J, K and L were stored for 30 days at 25° C./60% RH condition as well as 40° C./75% RH conditions. Under these conditions, baclofen remained solubilized and the compositions were clear without any recrystallization or precipitation.

Example 4

TABLE 7

| Ingredients | Composition M | N |
|---|---|---|
| | Quantity/batch | |
| Baclofen | 500 mg | 500 mg |
| HP-β-CD | — | 5000 mg |
| pH 3.5 Citrate Buffer USP | q.s. up to 100 mL | q.s. up to 100 mL |

The required amount of pH 3.5 citrate buffer solution (90 mL) was weighed and heated until the temperature reached between 60±5° C. The required quantity of HP-β-CD was added to the citrate buffer solution, and stirred until a clear solution was observed at 60±5° C. Next, the required amount of baclofen was added, and stirred until a clear solution was observed at 60±5° C. The solution was cooled to room temperature. The solution was adjusted to a total volume of 100 mL with a q.s. of pH 3.5 citrate buffer.

Samples of Composition M and N were stored for 30 days at 25° C./60% RH testing conditions as well as at 40° C./75% RH testing conditions. The baclofen remained solubilized and the compositions were clear without any recrystallization or precipitation.

Compositions M and N were also subjected to freeze thaw cycling and observed for any visible particles or crystals by physical observation. No visible particles were observed after 3 Freeze-Thaw cycles.

Further composition M was stored at 2° C.-8° C. and for 25° C./60% RH at least 5 months.

TABLE 8

| | Composition M | |
|---|---|---|
| Condition | 2-8° C. | 25° C./60% RH |
| Duration | 5 Months | 5 Months |
| Pack | HDPE | HDPE |
| Description | Clear solution | Clear solution |
| Impurity Profile | | |
| BRC A | 0.07 | 0.29 |
| Unknown impurity | 0.13 | 0.68 |
| Total impurity | 0.20 | 0.97 |

The composition M is both physically and chemically stable for at least 5 months, without visible particles and no significant increase in the total known (BRC A) and unknown impurities.

Example 5

TABLE 9

| Ingredients | Composition O Quantity/batch |
|---|---|
| Baclofen | 20.00 gm |
| HP-β-CD | 200.00 gm |
| Methyl Paraben | 8.00 gm |
| Propyl Paraben | 0.80 gm |
| Sucralose | 12.00 gm |
| Mixed Berry Flavor | 8.00 gm |
| Purified Water | q.s. to 4000 mL |

Composition O was prepared by taking 3680 mL of purified water in a manufacturing vessel and heated up to 60° C.±2° C. 200 gram of HP-β-CD was added to the above heated water with continuous mixing at a temperature of 60° C.±2° C. 20 gm of Baclofen was added to the obtained solution with continued stirring until baclofen get dissolved at a temperature of 60° C.±2° C. 8 gram of methyl paraben and 0.80 gram of propyl paraben were added to the above solution with continuous mixing, at a temperature of 58° C.±2° C. and mixing continued. The solution was cooled under continuous mixing until temperature reduced to 37° C.±2° C. 12 gram of sucralose and 8 gram of mixed berry flavour were added, with continuous mixing, at a temperature of 37° C.±2° C. The mixing was continued until everything gets dissolved. The final volume of the solution was adjusted to the 4000 mL using q.s. of purified water. The pH of final solution was 6.5.

TABLE 10

| | Composition O | | | | |
|---|---|---|---|---|---|
| Condition | Initial | Freeze Thaw Cycle | 2-8° C. | 40° C./75% RH | 40° C./75% RH |
| Duration | — | 3 Cycle | 2 Months | 1 Month | 2 Months |
| Pack | — | CT | HDPE | HDPE | HDPE |

TABLE 10-continued

| | Composition O | | | | |
|---|---|---|---|---|---|
| Description | Clear solution | Clear solution | Clear solution | Clear solution | Clear solution |
| | | | Impurity Profile | | |
| BRC A | 0.16 | NA | 0.16 | 0.24 | 0.33 |
| Unknown impurity | ND | NA | ND | ND | ND |
| Total impurity | 0.16 | NA | 0.16 | 0.26 | 0.33 |

Samples of Composition O were stored for 2 months at 2-8° C. condition as well as 40° C./75% RH conditions, baclofen remains solubilized and samples were found to be clear without any recrystallization or precipitation.

Example 6

TABLE 11

| Ingredients | Composition P Quantity/batch |
|---|---|
| Baclofen | 1.50 gm |
| SBE-β-CD | 9.00 gm |
| Methyl Paraben | 0.60 gm |
| Propyl Paraben | 0.06 gm |
| Sucralose | 0.90 gm |
| Mixed Berry Flavor | 0.60 gm |
| Purified Water | q.s. to 300 mL |

Composition P was prepared by taking 260 mL of purified water in a manufacturing vessel and heated up to 60° C.±2° C. 9 gram of SBE-β-CD was added to the above heated water with continuous mixing at a temperature of 60° C.±2° C. 1.50 gm of Baclofen was added to the obtained solution with continued stirring until baclofen get dissolved at a temperature of 60° C.±2° C. 0.60 gram of methyl paraben and 0.06 gram of propyl paraben were added to the above solution with continuous mixing, at a temperature of 58° C.±2° C. and mixing continued. The solution was cooled under continuous mixing until temperature reduce to 37° C.±2° C. 0.90 gram of sucralose and 0.60 gram of Mixed Berry Flavour were added, with continuous mixing, at a temperature of 37° C.±2° C. The mixing continued until everything gets dissolved. The final volume of the solution was adjusted to the 300 mL using q.s. of purified water. The pH of final solution was 6.5.

TABLE 12

| | Composition P | | |
|---|---|---|---|
| Condition | Initial | Freeze Thaw Cycle (2-8° C. followed by 40° C./75% RH) | 40° C./ 75% RH |
| Duration | — | 3 Cycle | 1 Month |
| Pack | — | CT | HDPE |
| Description | Clear solution | Clear solution | Clear solution |

TABLE 12-continued

| | Composition P | | |
|---|---|---|---|
| | Impurity Profile | | |
| BRC A | 0.16 | NA | 0.23 |
| Unknown impurity | ND | NA | ND |
| Total impurity | 0.17 | NA | 0.25 |

Composition P was stored for 30 days at 40° C./75% RH condition, baclofen remains solubilized and composition was found to be clear without any recrystallization or precipitation.

Example 7

TABLE 13

| | Composition | | |
|---|---|---|---|
| Ingredients | Q | R | S |
| | | Quantity/batch | |
| Baclofen | 20.00 gm | 2.50 gm | 2.50 gm |
| HP-β-CD | 200.00 gm | 25.00 gm | 25.00 gm |
| Methyl Paraben | 8.00 gm | 1.00 gm | 1.00 gm |
| Propyl Paraben | 0.80 gm | 0.10 gm | 0.10 gm |
| Sucralose | 12.00 gm | 1.50 gm | 1.50 gm |
| Mixed Berry Flavor | 8.00 gm | 1.00 gm | 1.00 gm |
| Purified Water | q.s. to 4000 mL pH 6.5 | q.s. to 500 mL pH 5.5 | q.s. to 500 mL pH 7.5 |

TABLE 14

| | Composition | | |
|---|---|---|---|
| | Q | R | S |
| Storage Condition | Stored at 40° C./75% RH for 1 Month | | |
| Description | Clear solution | Clear solution | Clear solution |
| BRC A | 0.24 | 0.23 | 0.23 |
| Unknown impurity | ND | ND | ND |
| Total impurity | 0.26 | 0.25 | 0.25 |

Required amount of water was added to suitable container, pH was adjusted by using 0.1N sodium hydroxide or 0.1N hydrochloric acid and heated until the temperature was 60±5° C. Required quantity of HP-β-CD was added, stirred until clear solution was observed at a temperature of 60±5°

C. Required amount of Baclofen was added to the above obtained clear solution and stirred until clear solution was observed at temperature of 60±5° C. Required amounts of methyl paraben and propyl paraben were added with continuous mixing at a temperature of 58° C.±2° C. and mixing continued. Solution was allowed to cool to room temperature. Specific quantities of sucralose and mixed berry flavor were added with continuous mixing at a temperature of 37° C.±2° C. and mixing continued until a clear solution was obtained. Solution was made up to the final volume.

Samples of Composition Q, R and S were stored for one month at 40° C./75% RH condition, baclofen remains solubilized and compositions were clear without any recrystallization or precipitation.

Example 8

TABLE 15

| Ingredient | Composition | | | | |
|---|---|---|---|---|---|
| | T | U | V | W | X |
| | Quantity (gram/batch) | | | | |
| Baclofen | 0.50 | 0.50 | 1.50 | 2.00 | 2.50 |
| HP-β-CD | — | — | — | — | — |
| Sodium Benzoate | — | — | — | — | 1.00 |
| Sucralose | — | — | — | — | 1.50 |
| Mixed Berry Flavor | — | — | — | — | 1.00 |
| pH 5 citrate buffer | q.s. to 100 mL | — | — | — | — |
| pH 6 citrate buffer | — | q.s. to 100 mL | — | — | — |
| pH 8 phosphate buffer | — | — | q.s. to 300 mL | — | — |
| pH 7 saline water | — | — | — | q.s. to 400 mL | — |
| pH 3.4 citrate buffer | — | — | — | — | q.s. to 500 mL |

TABLE 16

| | Composition | | | | |
|---|---|---|---|---|---|
| | T | U | V | W | X |
| pH | 5 | 6 | 8 | 7 | 3.4 |
| Storage Condition | Stored at 40° C./75% RH for 1 Month | | | | |
| Description | Unclear solution with fine particles | Unclear solution with fine particles | Fine particles observed in Solution | Fine particles observed in Solution | Clear solution |
| Impurity Profile | | | | | |
| BRC A | 0.32 | 0.20 | 0.70 | 0.18 | 0.61 |
| Unknown impurity | 0.68 | 0.35 | 0.02 | 0.02 | 1.60 |
| Total impurity | 2 | 0.55 | 0.72 | 0.20 | 2.11 |

Required amount of water was added to suitable container, pH was adjusted using citrate buffer or phosphate buffer or saline water and heated until the temperature was 60±5° C. Required amount of baclofen was added to the above step and stirred until clear solution was observed at a temperature of 60±5° C. Required amounts of sodium benzoate, was added with continuous mixing at temperature 58° C.±2° C. and mixing continued until get dissolved. Allow solution to cool to room temperature. Add specific quantities of sucralose and mixed berry flavor with continuous mixing at temperature 37° C.±2° C. and mixing continued until get dissolved. Make up the solution to the final volume.

Samples of Composition T, U, V, W & X were stored for one month at 40° C./75% RH condition, baclofen remained insolubilized in T, U, V, W and compositions were observed with clear particles, whereas baclofen is completely solubilized in composition X.

Thus, the present invention provides high-concentration, aqueous solutions of baclofen, which are stable under a variety of storage conditions and for extended periods of time.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

While compositions and methods are described herein in terms of "comprising" various components or steps, the compositions and methods can also "consist essentially of" or "consist of" the various components and steps.

The invention claimed is:

1. A liquid pharmaceutical composition, comprising baclofen, a solubilizer, and a pharmaceutically acceptable excipient selected from the group consisting of a sweetening agent, a flavoring agent, a preservative, an antioxidant, a viscosity modifier, a pH adjusting agent, a buffering agent, a coloring agent, a surfactant, and mixtures thereof, wherein baclofen is present at a concentration of about 2 mg/mL or more, wherein the pharmaceutical composition is an aqueous solution for oral administration, and wherein the liquid pharmaceutical composition is stable; and
   wherein the solubilizer is at least one of cyclodextrin or a cyclodextrin derivative selected from the group consisting of hydroxypropyl-β-cyclodextrin (HP-β-CD), methyl-β-cyclodextrin, sulfobutylether-β-cyclodextrin (SBE-β-CD), and hydroxypropyl-γ-cyclodextrin.

2. The liquid pharmaceutical composition according to claim 1, wherein baclofen is present at a concentration from about 5 mg/mL to about 10 mg/mL.

3. The liquid pharmaceutical composition according to claim 2, wherein the cyclodextrin or cyclodextrin derivative is present at a concentration of about 10 mg/mL to about 400 mg/mL, preferably from about 25 mg/mL to about 100 mg/mL, more preferably about 50 mg/mL.

4. The liquid pharmaceutical composition according to claim 2, wherein the weight ratio of cyclodextrin or cyclodextrin derivative to baclofen is from about 1:1 to about 80:1, preferably from about 5:1 to about 20:1, more preferably about 10:1.

5. The liquid pharmaceutical composition according to claim 1, wherein the liquid pharmaceutical composition has a pH in the range of about 5 to about 8, preferably between about 6 to about 7.

6. The liquid pharmaceutical composition according to the claim 1, wherein the composition is stable for at least 6 months at 40° C./75% RH.

7. The liquid pharmaceutical composition according to the claim 1, wherein the composition is stable for at least 12 months at about 2° C. to 8° C.

8. The pharmaceutical composition according to claim 1, wherein a level of (4-(4-chlorophenyl)-2-pyrrolidinone is less than about 2% (w/w), preferably less than about 1.5% (w/w), more preferably less than about 1% (w/w) as measured by HPLC.

9. A pharmaceutical composition according to claim 1, comprising:
   (i) about 5 mg/mL of baclofen;
   (ii) about 50 mg/mL of cyclodextrin or a cyclodextrin derivative;
   (iii) about 2 mg/mL of a preservative;
   (iv) water;
   (v) a flavouring agent; and
   (vi) a sweetener.

10. A process for the preparation of a stable, liquid pharmaceutical formulation for oral administration comprising baclofen according to claim 1, the process comprising the steps of:
   a) heating water to a temperature of up to about 60° C.;
   b) adding cyclodextrin or the cyclodextrin derivative to the water to form a first solution;
   c) stirring the first solution to obtain a first clear solution;
   d) adding baclofen to the first clear solution to form a second solution;
   e) stirring the second solution to obtain a second clear solution;
   f) optionally, adding the pharmaceutically acceptable excipient; and
   g) stirring to obtain a final clear solution.

11. A method for managing, treating or alleviating the signs and symptoms of spasticity resulting from multiple sclerosis, spinal cord damage or spinal cord disease in a patient by orally administering an effective amount of a liquid pharmaceutical composition according to claim 1.

12. The method of claim 11, wherein the patient is an adult, pediatric or geriatric patient.

13. A liquid pharmaceutical composition, comprising baclofen, a cyclodextrin, water, and a pharmaceutically acceptable excipient selected from the group consisting of a sweetening agent, a flavoring agent, a preservative, an antioxidant, a viscosity modifier, a pH adjusting agent, a buffering agent, a coloring agent, a surfactant, and mixtures thereof, wherein baclofen is present at a concentration of about 2 mg/mL or more, wherein the pharmaceutical composition is an aqueous solution for oral administration.

14. The liquid pharmaceutical composition according to the claim 13, wherein the composition is stable for at least 6 months at 40° C./75% RH.

* * * * *